United States Patent
Anderson et al.

(10) Patent No.: US 12,096,917 B2
(45) Date of Patent: Sep. 24, 2024

(54) TIP CAMERA SYSTEMS AND METHODS FOR VITREORETINAL SURGERY

(71) Applicant: Alcon Inc., Fribourg (CH)

(72) Inventors: Joshua Anderson, Keller, TX (US); Paul Hallen, Colleyville, TX (US)

(73) Assignee: Alcon Inc., Fribourg (CH)

( * ) Notice: Subject to any disclaimer, the term of this patent is extended or adjusted under 35 U.S.C. 154(b) by 99 days.

(21) Appl. No.: 17/024,336

(22) Filed: Sep. 17, 2020

(65) Prior Publication Data
US 2021/0093177 A1 Apr. 1, 2021

Related U.S. Application Data

(60) Provisional application No. 62/906,794, filed on Sep. 27, 2019.

(51) Int. Cl.
| | |
|---|---|
| *A61B 1/05* | (2006.01) |
| *A61B 1/00* | (2006.01) |
| *A61B 1/06* | (2006.01) |
| *A61B 1/07* | (2006.01) |
| *G02B 27/01* | (2006.01) |

(52) U.S. Cl.
CPC ............ *A61B 1/05* (2013.01); *A61B 1/00045* (2013.01); *A61B 1/00174* (2013.01); *A61B 1/0684* (2013.01); *A61B 1/07* (2013.01); *G02B 27/017* (2013.01); *A61B 1/00009* (2013.01)

(58) Field of Classification Search
CPC ....... A61B 1/0005; A61B 1/07; A61B 90/361; A61B 2034/2057; A61B 2090/3614; A61B 2090/371; A61B 2034/2065
See application file for complete search history.

(56) References Cited

U.S. PATENT DOCUMENTS

| | | | |
|---|---|---|---|
| 5,217,453 A * | 6/1993 | Wilk ................... | A61B 5/0022 606/7 |
| 2009/0182312 A1* | 7/2009 | Gertner ................ | A61F 9/009 606/4 |
| 2016/0235276 A1* | 8/2016 | Steffen ................ | A61B 90/20 |
| 2017/0059848 A1* | 3/2017 | Haraguchi ......... | G02B 23/2469 |
| 2018/0063387 A1* | 3/2018 | Wei ..................... | A61B 1/00016 |
| 2019/0038364 A1* | 2/2019 | Enoki .................. | A61B 34/20 |
| 2019/0192232 A1* | 6/2019 | Altmann .............. | A61B 5/064 |
| 2020/0188668 A1* | 6/2020 | Grossoehmichen ........ A61N 1/0541 |
| 2021/0015350 A1* | 1/2021 | Butte ................... | G02B 21/16 |
| 2021/0330396 A1* | 10/2021 | Govari ................ | A61B 5/6821 |
| 2022/0257098 A1* | 8/2022 | Miyachi .............. | G02B 23/26 |

* cited by examiner

*Primary Examiner* — Michael J Carey
*Assistant Examiner* — Stephen Floyd London

(57) ABSTRACT

The present disclosure provides a tip camera system that includes a probe including a probe body and a probe tip, an optical fiber light source, and an optical fiber positioned within the probe body that emits light at the probe tip to illuminate a local view of an interior of an eye. The system further includes a tip camera positioned in the probe tip and includes a sensor that detects light emitted by the optical fiber and reflected off the interior of the eye, and that sends a signal corresponding to the detected light to a processor. The system also includes an image processing system that includes the processor and that executes instructions to produce a tip camera digital image of the eye. The system also includes a digital display that displays the tip camera digital image of the eye.

16 Claims, 9 Drawing Sheets

TIP CAMERA SYSTEMS AND METHODS FOR VITREORETINAL SURGERY

TECHNICAL FIELD

The present disclosure relates to vitreoretinal surgery and surgical equipment, and more specifically, to a tip camera system to improve visualization for vitreoretinal surgery and associated methods.

BACKGROUND

Ophthalmic surgery is surgery performed on the eye or any part of the eye. Ophthalmic surgery saves and improves the vision of tens of thousands of patients every year. However, given the sensitivity of vision to even small changes in the eye and the minute and delicate nature of many eye structures, ophthalmic surgery is difficult to perform and the reduction of even minor or uncommon surgical errors or modest improvements in accuracy of surgical techniques can make an enormous difference in the patient's vision after the surgery.

One type of ophthalmic surgery, vitreoretinal surgery, encompasses various delicate procedures involving internal portions of the eye, such as the vitreous humor, the retina, and the vitreoretinal membrane. Different vitreoretinal surgical procedures are used, sometimes with lasers, to improve visual sensory performance in the treatment of many eye diseases, including epimacular membrane, diabetic retinopathy, vitreous hemorrhage, macular hole, detached retina, and complications of cataract surgery, among others.

During ophthalmic surgery, such as vitreoretinal surgery, an ophthalmologist typically uses a non-electronic, optical, surgical microscope with oculars to view a magnified image of the eye undergoing surgery. More recently, vitreoretinal surgeons may use an ocular-free digital image system to aid visualization during vitreoretinal surgery. These systems may include a three-dimensional (3D) high dynamic range ("HDR") camera system with a pair of two-dimensional (2D) complementary metal-oxide-semiconductor (CMOS) single chip or three-chip sensors that allows the surgeon to view the retina on a display screen using polarized glasses, digital oculars or a head-mounted display. The display screen provides relief from having to view the surgery using oculars and allows others in the operating room to see exactly as the surgeon does. The system also allows for improved images under high magnification, and increased depth of field compared to a conventional optical, analog surgical microscope, which allow for improved visualization of the eye.

SUMMARY

The present disclosure provides a tip camera system that improves visualization for vitreoretinal surgery and associated methods. The tip camera system includes a probe including a probe body and a probe tip, an optical fiber light source, and an optical fiber positioned within the probe body, and that emits light at the probe tip to illuminate a local view of an interior of an eye. The tip camera system also includes a tip camera positioned in the probe tip that includes a sensor that detects light emitted by the optical fiber and reflected off the interior of the eye, and that sends a signal corresponding to the detected light to a processor. The tip camera system also includes an image processing system that includes the processor, and that executes instructions to produce a tip camera digital image of the eye. The tip camera system also includes a digital display that displays the tip camera digital image of the eye.

The tip camera system and its methods of use may include the following additional features: i) the system may include a visible light illumination source that emits light to illuminate an aerial view of the eye, and an exterior camera that detects light emitted by the visible light illumination source and reflected off the eye and sends a signal corresponding to the detected light to the processor. The image processing system may execute instructions to produce an exterior camera digital image of the eye, and the digital display may be a picture-in-picture display that displays the tip camera digital image of the eye and the exterior camera digital image of the eye concurrently; ii) the probe may be a vitrectomy probe or an infusion probe; iii) the probe tip may be inserted into the eye; iv) the sensor may be a complementary metal-oxide semiconductor (CMOS) sensor, a monochrome image sensor, a color image sensor, or any combination thereof; v) the sensor may have dimensions in the range of from about 0.4 to about 0.7 mm; vi) the optical fiber light source may be a laser source, a narrowband laser source, a broadband laser source, a supercontinuum laser source, an incandescent light bulb, a halogen light bulb, a metal halide light bulb, a xenon light bulb, a mercury vapor light bulb, a light emitting diode (LED), a laser engine, other suitable sources, or any combination thereof; vii) the digital display may be a picture-in-picture display, a digital display, a screen, a head up display, a head mounted display, or any combination thereof; viii) the tip camera system may be a component of a NGENUITY® 3D Visualization System (Novartis AG Corp., Switzerland).

The present disclosure further provides a tip camera system that includes an endoscope; an optical fiber light source, and an optical fiber positioned within the endoscope that emits light at a tip of the endoscope to illuminate a local view of an interior of an eye. The tip camera system also includes a camera including a sensor that detects light reflected off the interior of the eye and propagated by the optical fiber, and that sends a signal corresponding to the detected light to a processor. The tip camera system also includes an image processing system that includes the processor and executes instructions to produce an endoscope digital image of the eye. The tip camera system also includes a digital display that displays the endoscope digital image of the eye.

The tip camera system and its methods of use may include the following additional features: ix) the system may further include a visible light illumination source that emits light to illuminate an aerial view of the eye, and an exterior camera that detects light emitted by the visible light illumination source and reflected off the eye, and that sends a signal corresponding to the detected light to the processor. The image processing system may execute instructions to produce an exterior camera digital image of the eye, and the digital display may be a picture-in-picture display that displays the endoscope digital image of the eye and the exterior camera digital image of the eye concurrently; x) the optical fiber may include image fibers and illumination fibers; xi) the endoscope may be inserted into the eye; xii) the sensor may be a complementary metal-oxide semiconductor (CMOS) sensor, a charge-coupled device (CCD) sensor, a monochrome image sensor, a color image sensor, or any combination thereof; xiii) the optical fiber light source may be a laser source, a narrowband laser source, a broadband laser source, a supercontinuum laser source, an incandescent light bulb, a halogen light bulb, a metal halide light bulb, a xenon light bulb, a mercury vapor light bulb, a light emitting diode (LED), a laser engine, other suitable sources, or any combination thereof; xiv) the digital display may be a picture-in-picture display, a digital display, a screen, a head up display, a head mounted display, or any combination thereof; xv) the system may be a component of a NGENUITY® 3D Visualization System (Novartis AG Corp., Switzerland).

The present disclosure further provides a method for viewing a local view and an aerial view of the eye concurrently by using an optical fiber that includes illumination fibers to illuminate a local view of an eye with light; using a camera to capture a digital image of the local view of the eye; using a visible light illumination source to illuminate an aerial view of the eye with light; using an exterior camera to capture a digital image of the aerial view of the eye; and using a picture-in-picture display to view the digital image of the local view of the eye and the digital image of the aerial view of the eye concurrently. The optical fiber may be positioned inside a probe that includes a probe body and a probe tip; the camera may be a tip camera positioned in the probe tip; and the tip camera may capture a tip camera digital image of the local view of the eye. The optical fiber may be positioned inside an endoscope and further include image fibers; and the camera may detect light propagated by the image fibers and capture an endoscope digital image of the local view of the eye.

Aspects of the tip camera system and its methods of use may be combined with one another unless clearly mutually exclusive. In addition, the additional features of the tip camera system and its associated methods described above may also be combined with one another unless clearly mutually exclusive.

BRIEF DESCRIPTION OF THE DRAWINGS

For a more complete understanding of the present disclosure and its features and advantages, reference is now made to the following description, taken in conjunction with the accompanying drawings, which are not to scale, in which like numerals refer to like features, and in which.

DETAILED DESCRIPTION

Figure 1:
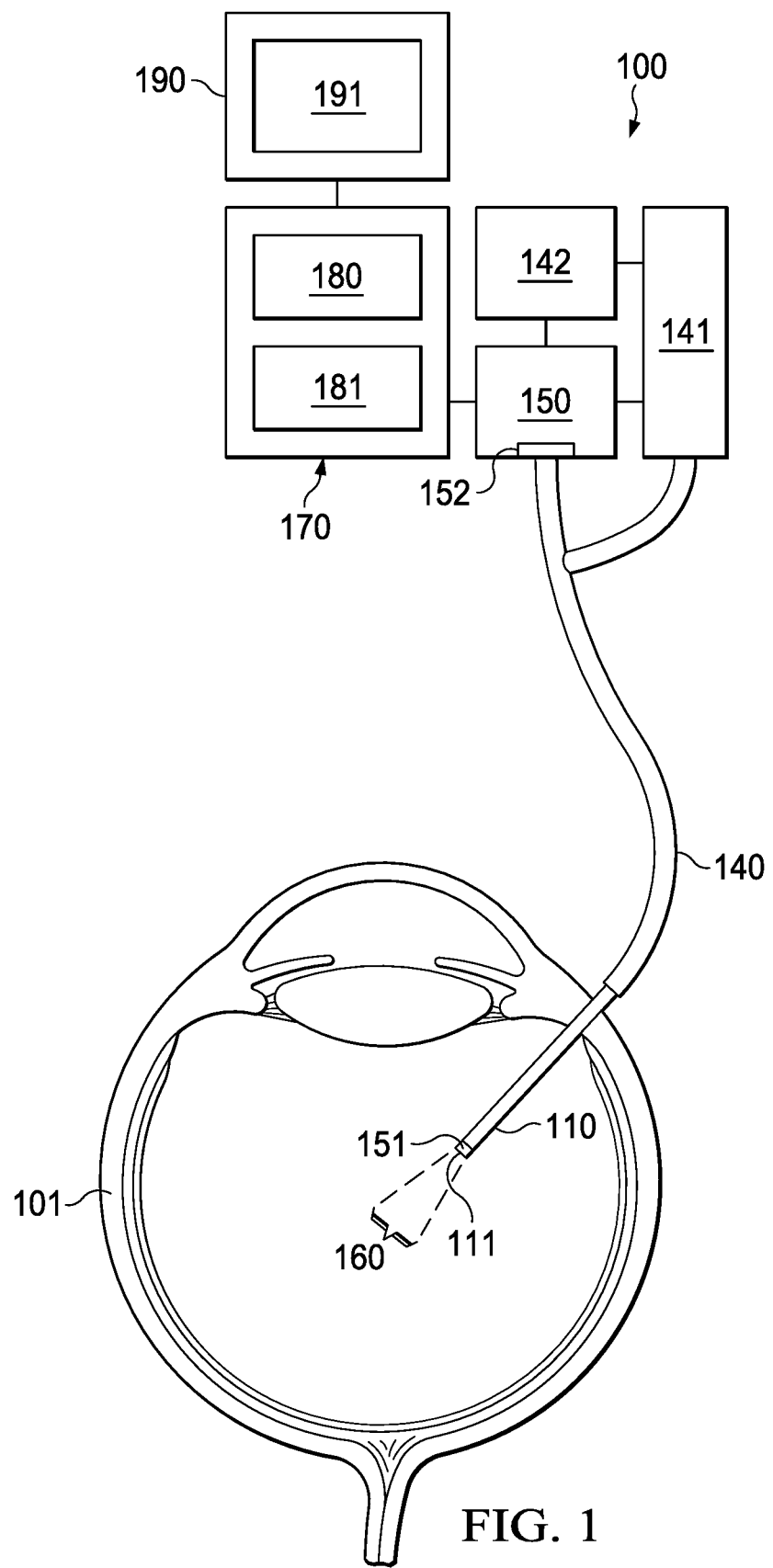
FIG. 1 is a schematic representation of a tip camera system, including an endoscope, an optical fiber, an optical fiber light source, a camera, an image processing system, and a digital display.

The present disclosure provides systems including a tip camera to improve visualization for vitreoretinal surgery and associated methods.

Vitreoretinal surgeons face unique challenges when visualizing the internal portions of the eye. For example, any view obtained through the patient's pupil is subject to optical aberration. Optical aberration may be caused by eye diseases or prior surgery causing corneal asphericity or intraocular lens implants which lead to an aberrated image viewed by the surgeon. Spherical aberration may be caused by dilation of the pupil, oblique viewing to visualize the peripheral retina, cataract, intraocular lenses, and corneal asphericity. Chromatic aberration, which may be lateral or axial, may be caused by the failure of the eye's optical system or retinal visualization system to focus different colors to the same focal point or plane. Aberration may interfere with the ability of the surgeon to visualize the interior of the eye and make surgery more difficult. In analog systems there are very limited ways to correct for the effect of aberrations, and many are simply uncorrectable. Digital visualization systems do allow for various corrective measures, which may improve the image presented to the surgeon and others assisting with vitreoretinal surgery. However, current systems and methods are not able to visualize the eye in cases where aberrations or defects partially or fully prevent light entering or leaving the interior of the eye. These may include instances where the cornea of an eye is cloudy, which may be caused by a long surgical procedure or an eye defect, instances where the lens in the eye is cloudy, which may be caused by a cataract, or when there is blood in the eye. In such cases, vitreoretinal surgery may have increased risk of complications, or may even be impossible to complete.

The tip camera systems and methods of the present disclosure may provide for faster, safer, and more efficient surgical procedures by improving visualization for vitreoretinal surgery. The systems and methods of the present disclosure may improve the ability to see the interior of the eye as compared to current systems and methods by including an endoscope or tip camera that may be inserted into the eye. The tip camera systems and methods disclosed herein may improve visualization for vitreoretinal surgery as compared to current systems and methods by providing a local view of the interior of the eye, which may include a close up view of the macula, vitreous humor, or other areas of the interior of eye. The tip camera systems and methods as described herein may improve visualization for vitreoretinal surgery as compared to current systems and methods by allowing the surgeon to visualize the interior of the eye in cases where aberrations or defects partially or fully prevent light entering or leaving the interior of the eye with current systems and methods. The tip camera systems and methods disclosed herein may improve visualization for vitreoretinal surgery as compared to current systems and methods by providing a local view and an aerial view of the eye concurrently.

Referring now to FIG. 1, tip camera system 100 may include endoscope 110, optical fiber 140, optical fiber light source 141 and camera 150. Tip camera system 100 may provide a local view of the interior of eye 101 to improve visualization for vitreoretinal surgery. Optical fiber 140 may be positioned within endoscope 110, and may extend to the tip 111 of endoscope 110. Endoscope 110 may be inserted into eye. Optical fiber 140 may be positioned such that it illuminates a local area of eye 101, and may be positioned within a cannula of an ophthalmic illumination apparatus. The cannula may be inserted into eye 101, and may be positioned such that a desired area of the interior of eye 101 is illuminated. Optical fiber 140 may include image fibers and illumination fibers. For example, optical fiber 140 may include about 30,000 image fibers and about 40 illumination fibers. Alternatively, optical fiber 140 may include any suitable number of image fibers and illumination fibers to provide a local view of the interior of eye 101 using endoscope 110.

Optical fiber 140 may be coupled to optical fiber light source 141. The illumination fibers in optical fiber 140 may propagate an illumination beam using light from optical fiber light source 141. Optical fiber 140 may emit light at the tip 111 of endoscope 110 to illuminate the interior of eye 101. The view illuminated by optical fiber 140 may be local view of the eye 160. Optical fiber light source 141 may be a laser source, a narrowband laser source, a broadband laser source, a supercontinuum laser source, an incandescent light bulb, a halogen light bulb, a metal halide light bulb, a xenon light bulb, a mercury vapor light bulb, a light emitting diode (LED), a laser engine, other suitable sources, or any combination thereof.

Endoscope 110 may include lens 151. Lens 151 may be a spherical lens or may be an aspherical lens. Lens 151 may be a fixed focal length lens, and may give a narrow field of view. Lens 151 may have any focal length appropriate to obtain a suitable local view of the eye 160. Local view of the eye 160 may include a close up view of the macula, vitreous humor, or other areas of the interior of eye 101. Light reflected off the interior of eye 101, which may be light emitted by the illumination fibers in optical fiber 140, may travel through lens 151, propagate through the image fibers in optical fiber 140, and may be detected by camera 150. Alternatively, endoscope 110 may be an analog endoscope (not shown), and light propagated by optical fiber 140 may be directed into an eyepiece. Endoscope 110 may also include an eyepiece in addition to camera 150.

Camera 150 may include camera sensor 152. Camera sensor 152 may be a complementary metal-oxide semiconductor (CMOS) sensor or a charge-coupled device (CCD) sensor. Camera 150 may be a monochrome camera, or may be a color camera, and camera sensor 152 may be a monochrome image sensor or may be a color image sensor. Camera sensor 152 may capture a digital image using light propagated by optical fiber 140, which may be light reflected off the interior of eye 101. Camera sensor 152 may capture a digital image of eye 101, which may be endoscope digital image of the eye 191. Endoscope digital image of eye 191 may include local view of the eye 160.

Optical fiber 140, optical fiber light source 141, camera 150, and camera sensor 152 may be controlled by control device 142. For example, control device 142 may adjust the intensity of optical fiber light source 141, the sensitivity of camera sensor 152, or any combination thereof. Although FIG. 1 illustrates a single endoscope 110 in tip camera system 100, tip camera system may include multiple endoscopes 110, optical fibers 140, cameras 150 and camera sensors 152. In this case, the multiple endoscopes 110 may be inserted into multiple positions of eye 101 to provide multiple endoscope digital images of the eye 191.

Tip camera system 100 may include image processing system 170. Digital images captured by camera sensor 152 may be processed by image processing system 170. Image processing system 170 may include processor 180. Camera sensor 152 may detect light reflected off the interior of eye 101 and propagated by optical fiber 140 and send a signal corresponding to the detected light to processor 180. Processor 180 may execute instructions to produce endoscope digital image of the eye 191.

Processor 180 may include, for example, a field-programmable gate array (FPGA), a microprocessor, a microcontroller, a digital signal processor (DSP), a graphics processing unit (GPU), an application specific integrated circuit (ASIC), or any other digital or analog circuitry configured to interpret and/or execute program instructions and/or process data.

Processor 180 may include any physical device able to store and/or execute instructions. Processor 180 may execute processor instructions to implement at least a portion of one or more systems, one or more flow charts, one or more processes, and/or one or more methods described herein. For example, processor 180 may execute instructions to produce the image of eye 101. Processor 180 may be configured to receive instructions from memory medium 181. In one example, processor 180 may include memory medium 181. In another example, memory medium 181 may be external to processor 180. Memory medium 181 may store the instructions. The instructions stored by memory medium 181 may be executable by processor 180 and may be configured, coded, and/or encoded with instructions in accordance with at least a portion of one or more systems, one or more flowcharts, one or more methods, and/or one or more processes described herein.

A FPGA may be may be configured, coded, and/or encoded to implement at least a portion of one or more systems, one or more flow charts, one or more processes, and/or one or more methods described herein. For example, the FPGA may be configured, coded, and/or encoded to produce an image of the interior of eye 101. An ASIC may be may be configured to implement at least a portion of one or more systems, one or more flow charts, one or more processes, and/or one or more methods described herein. For example, the ASIC may be configured, coded, and/or encoded to produce an image of the interior of eye 101. A DSP may be may be configured, coded, and/or encoded to implement at least a portion of one or more systems, one or more flow charts, one or more processes, and/or one or more methods described herein. For example, the DSP may be configured, coded, and/or encoded to produce an image of the interior eye 101.

A single device may include processor 180 and image processing system 170, or processor 180 may be separate from image processing system 170. In one example, a single computer system may include processor 180 and image processing system 170. In another example, a device may include integrated circuits that may include processor 180 and image processing system 170. Alternatively, processor 180 and image processing system 170 may be incorporated into a surgical console.

Processor 180 may interpret and/or execute program instructions and/or process data stored in memory medium 181. Memory medium 181 may be configured in part or whole as application memory, system memory, or both. Memory medium 181 may include any system, device, or apparatus configured to hold and/or house one or more memory devices. Each memory device may include any system, any module or any apparatus configured to retain program instructions and/or data for a period of time (e.g., computer-readable media). One or more servers, electronic devices, or other machines described may include one or more similar such processors or memories that may store and execute program instructions for carrying out the functionality of the associated machine.

Tip camera system 100 may include digital display 190. Digital display 190 may include any type of screen or projector able to display a digital image of the eye with sufficient resolution to be usable in ophthalmic surgery. For instance, it may include any type of screen or projector used in connection with ophthalmic surgery, including displays of the type used in conventional vitreoretinal surgical systems that present digital images. Digital display 190 may display endoscope digital image of the eye 191. This may improve visualization for vitreoretinal surgery by providing a local view of the eye, which may be local view of the eye 160. Digital display 190 may display a single image, or two images for stereoscopic viewing. Digital display 190 may be a digital display, a screen, a head up display, a head mounted display, or any combination thereof, and may also include multiple displays. Digital display 190 may be a flat panel display or an ultra-high-definition 3D flat panel display. Digital display 190 may be a 3D organic light-emitting diode (OLED) surgical display. The images displayed on digital display 190 may be viewed through a pair of passive, circular polarized glasses, such as the NGENUITY® 3D Visualization System (Novartis AG Corp., Switzerland). Digital display 190 may be a component of a Digitally Assisted Vitreoretinal Surgery ("DAVS").

Digital display 190 may display endoscope digital image of the eye 191 generated by processor 180 or another processor and other information generated by processor 180 or another processor. Such information may include graphic or textual information, such as surgical parameters, surgical modes, flow rates, intraocular pressure, endoscopic video, OCT images, warnings, digital images, color coding or augmented reality information. Processor 180 may reformat video made using camera 150 for display on digital display 190, which may be viewed with circularly polarized glasses, digital oculars, or using a head mounted display.

Figures 2A, 2B:
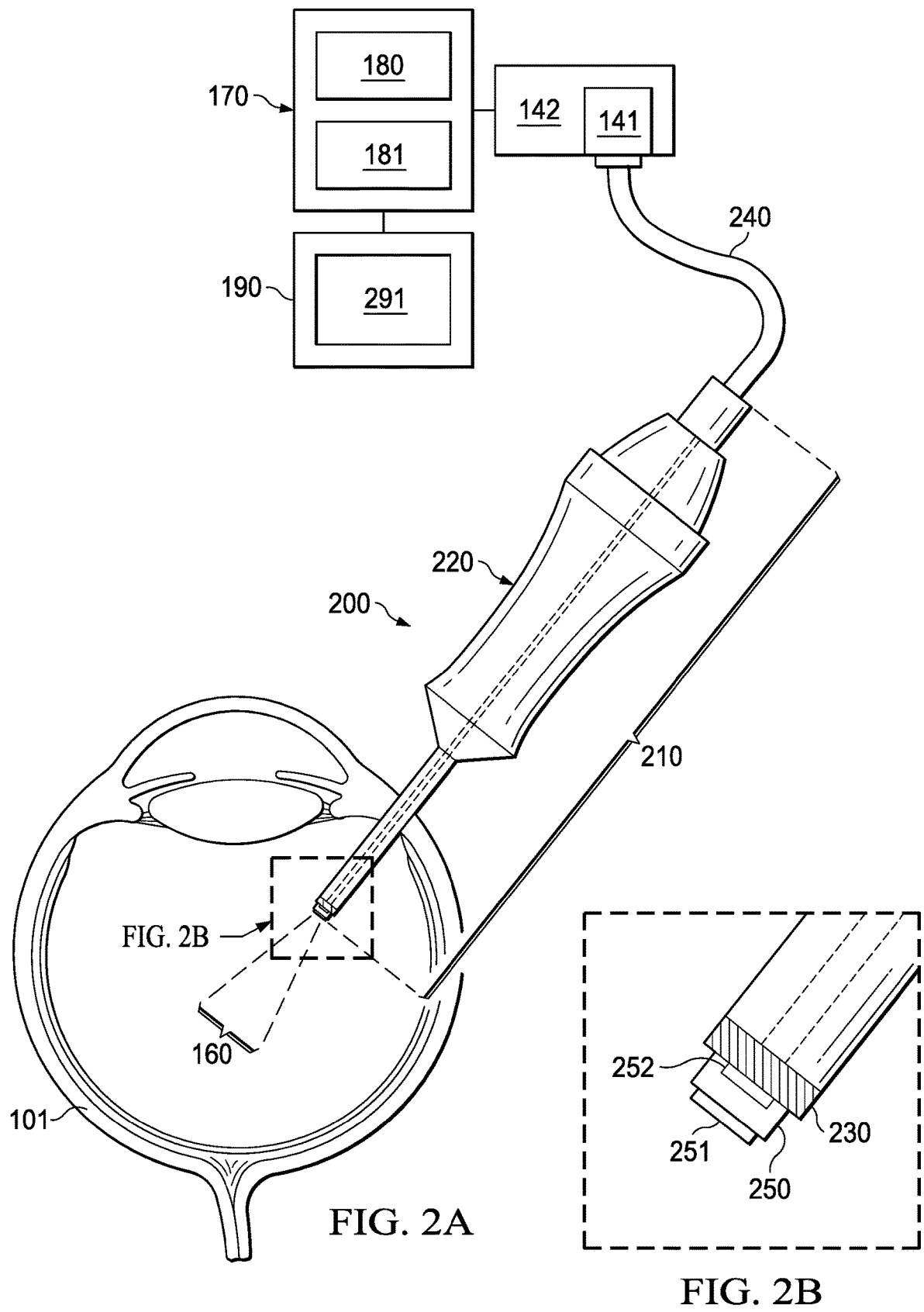
FIG. 2A is a schematic representation of a tip camera system, including a probe, a tip camera; an optical fiber, an optical fiber light source, an image processing system, and a digital display.
FIG. 2B is a detailed schematic representation of the distal portion of the probe and the tip camera.

In an alternative example, endoscope 110 may be substituted for probe 210 and tip camera 250 in tip camera system 200, as depicted in FIG. 2A. Referring now to FIG. 2A, tip camera system 200 may include probe 210, optical fiber 240, optical fiber light source 141, and tip camera 250. Tip camera system 200 may provide a local view of the interior of eye 101 to improve visualization for vitreoretinal surgery. Probe 210 may include probe body 220 and probe tip 230. Optical fiber 240 may be positioned within probe body 220 and may extend to probe tip 230. Probe 210 may be a vitrectomy probe or an infusion probe. Probe tip 230 may be inserted in eye 101. Alternatively, probe tip 230 and a suitable length of probe body 220 may be inserted into eye 101. Probe 210 may be positioned such that optical fiber 240 may illuminate a local area of eye 101. Probe 210 may be positioned within a cannula of an ophthalmic illumination apparatus. The cannula may be inserted into eye 101, and may be positioned such that a desired area of the interior of eye 101 is illuminated. Optical fiber 240 may include illumination fibers. For example, optical fiber 240 may include about 40 illumination fibers. Alternatively, optical fiber 240 may include any suitable number illumination fibers to provide a local view of the interior of eye 101 using tip camera 250. FIG. 2B is a detailed schematic representation of the distal portion of the probe 210 and the tip camera 250.

Optical fiber 240 may be coupled to optical fiber light source 141. The illumination fibers in optical fiber 240 may propagate an illumination beam using light from optical fiber light source 141. Optical fiber 240 may emit light at probe tip 230 to illuminate the interior of eye 101. The view illuminated by optical fiber 240 may be local view of the eye 160.

Tip camera 250 may be positioned in probe tip 230. Tip camera 250 may capture tip camera digital image of the eye 291, which may include local view of the eye 160. Tip camera 250 may include lens 251 and tip camera sensor 252. Lens 251 may be a spherical lens or may be an aspherical lens. Lens 251 may be a fixed focal length lens, and may give a narrow field of view. Lens 251 may have any focal length appropriate to obtain a suitable local view of the eye 160. Local view of the eye 160 may include a close up view of the macula, vitreous humor, or other areas of the interior of eye 101. Light reflected off the interior of eye 101, which may be light emitted by the illumination fibers in optical fiber 240, may travel through lens 251 and may be detected by tip camera sensor 252.

Tip camera sensor 252 may be a complementary metal-oxide semiconductor (CMOS) sensor. Tip camera sensor 252 may have dimensions in the range of from about 0.4 to about 0.7 mm. Tip camera sensor may have a pixel array of about 250 pixels×250 pixels or less. Tip camera 250 may be a monochrome camera, or may be a color camera, and tip camera sensor 252 may be a monochrome image sensor or may be a color image sensor. The illumination fibers in optical fiber 240 may be packed around tip camera sensor 252 to provide a cylindrical shape. This may allow probe tip 230 to be more easily inserted into eye 101. Tip camera sensor 252 may capture a digital image using light emitted by optical fiber 240, which may be light reflected off the interior of eye 101. Tip camera sensor 252 may capture a digital image of eye 101, which may be tip camera digital image of the eye 291. Tip camera digital image of eye 291 may include local view of the eye 160.

Optical fiber light source 141, optical fiber 240, tip camera 250, and tip camera sensor 252 may be controlled by control device 142. For example, control device 142 may adjust the intensity of optical fiber light source 141, the sensitivity of tip camera sensor 252, or any combination thereof.

Tip camera system 200 may include image processing system 170. Digital images captured by tip camera sensor 252 may be processed by image processing system 170. Image processing system 170 may include processor 180. Tip camera sensor 252 may detect light emitted by optical fiber 240 and reflected off the interior of eye 101 and send a signal corresponding to the detected light to processor 180. Processor 180 may execute instructions to produce a tip camera digital image of the eye 291.

Tip camera system 200 may include digital display 190. Digital display 190 may display tip camera digital image of the eye 291. This may improve visualization for vitreoretinal surgery by providing a local view of the eye, which may be local view of the eye 160.

Digital display 190 may display digital image of the eye 291 generated by processor 180 or another processor and other information generated by processor 180 or another processor. Such information may include graphic or textual information, such as surgical parameters, surgical modes, flow rates, intraocular pressure, endoscopic video, OCT images, warnings, digital images, color coding or augmented reality information. Processor 180 may reformat video made using tip camera 250 for display on digital display 190, which may be viewed with circularly polarized glasses, digital oculars, or using a head mounted display.

Figure 3A:
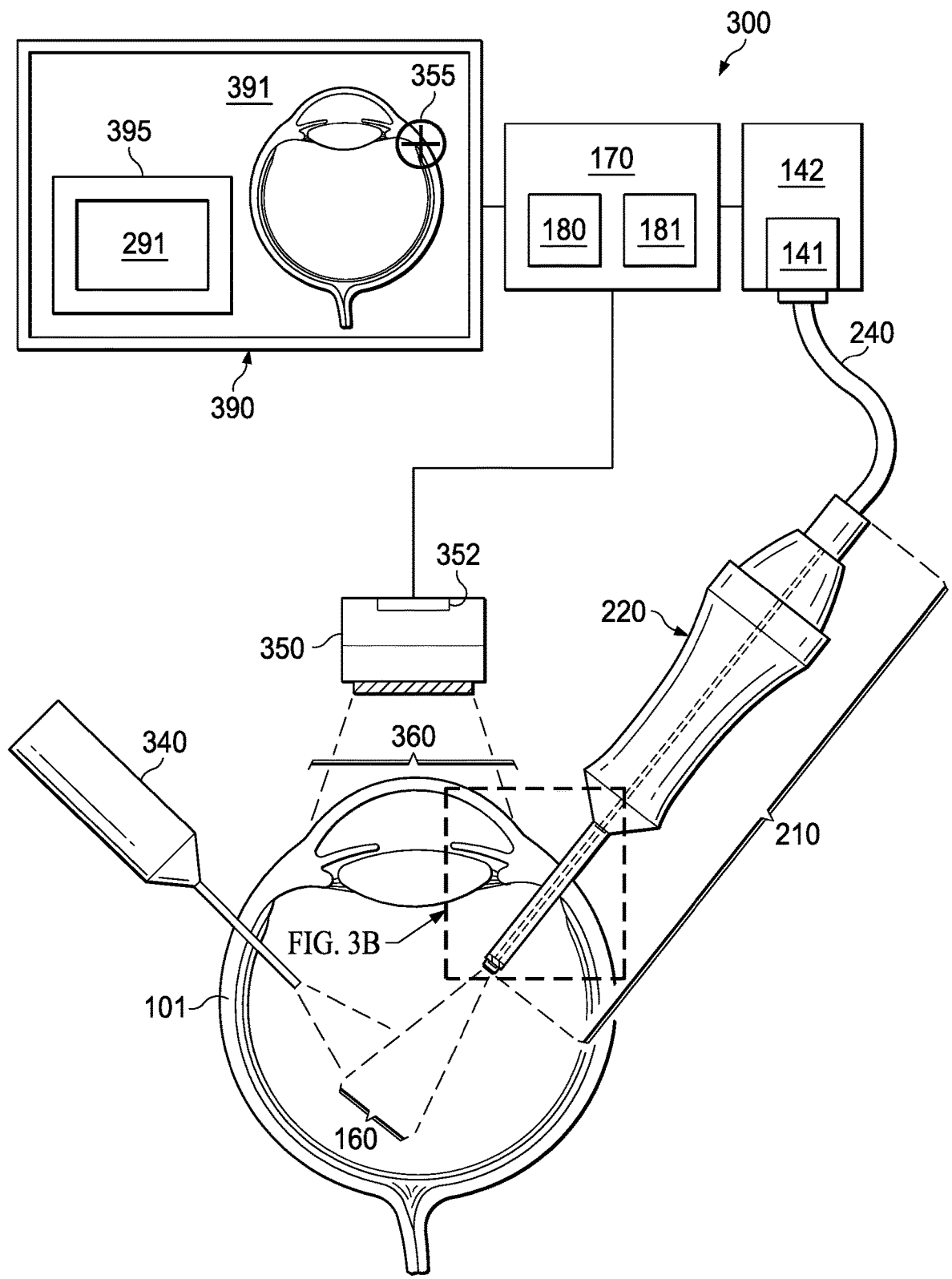
FIG. 3A is a schematic representation of a tip camera system, including a probe, a tip camera; an optical fiber, an optical fiber light source, an exterior camera, an image processing system, and a picture-in-picture display.
Figure 3B:
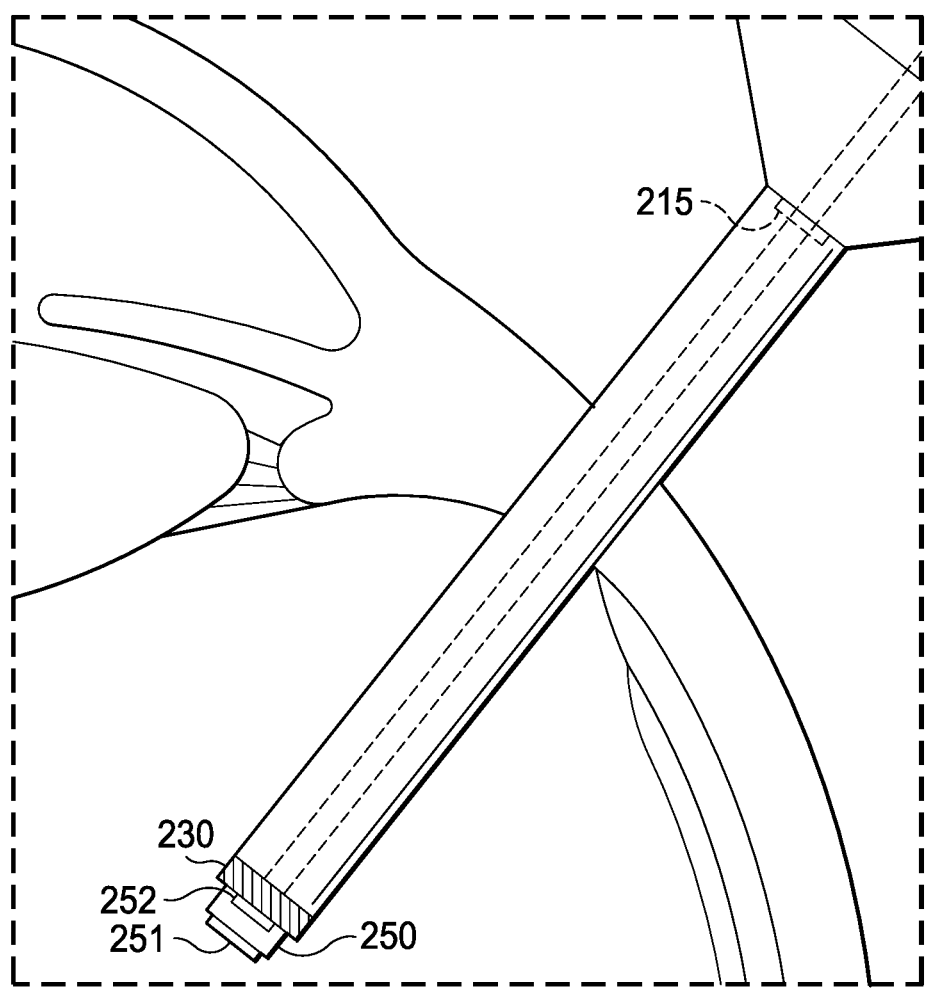
FIG. 3B is a detailed schematic representation of the distal portion of the probe and the tip camera.

Tip camera system 100 or tip camera system 200 may be used in conjunction with exterior camera 350 in tip camera system 300, as shown in FIG. 3. This may improve visualization for vitreoretinal surgery by providing a surgeon with a local view and an aerial view of the eye concurrently. Although exterior camera 350 is depicted with tip camera system 200 in FIG. 3A, it may equally be used in conjunction with tip camera system 100. Exterior camera 350 may capture exterior camera digital image of the eye 391, which may include aerial view of the eye 360. Exterior camera digital image of the eye 391 may be an image with a wider field of view compared to endoscope digital image of the eye 191 or tip camera digital image of the eye 291. Exterior camera digital image of the eye 391 may include digital images of the macula, vitreous humor, retina, vitreoretinal pathology, or other areas of the eye, or it may simply provide a digital image of lower magnification compared to endoscope digital image of the eye 191 or tip camera digital image of the eye 291. Exterior camera 350 may also be configured to provide a stereoscopic digital image of eye 101 (not shown). Exterior camera 350 may be a digital camera, an HDR camera, a 3D camera, a surgical camera, or any combination thereof. Exterior camera 350 may also be a camera coupled to a microscope. Exterior camera 350 may replace the oculars on a microscope. Exterior camera 350 may be a component of a Digitally Assisted Vitreoretinal Surgery ("DAVS") system, or may be a component of a NGENUITY® 3D Visualization System (Novartis AG Corp., Switzerland). FIG. 3B is a detailed schematic representation of the distal portion of the probe and the exterior camera 350.

Exterior camera 350 may include exterior camera image sensor 352, which may be a complementary metal-oxide semiconductor (CMOS) sensor or a charge-coupled device (CCD) sensor. Exterior camera 350 may be a monochrome camera, or may be a color camera, and exterior camera image sensor 352 may be a monochrome image sensor or may be a color image sensor. Tip camera system 300 may include visible light illumination source 340, which may provide an illumination source for exterior camera 350. Visible light illumination source 340 may be an endoilluminator. Visible light illumination source 340 may include a xenon source, a white LED light source, or any other suitable visible light source. Visible light illumination source 340 may illuminate an interior structure of the eye. Visible light illumination source 340 may emit light to illuminate aerial view of the eye 360.

Digital images captured by tip camera sensor 252 and exterior camera image sensor 352 may be processed by image processing system 170. Exterior camera 350 may detect light emitted by visible light illumination source 340 and reflected off eye 101 using exterior camera image sensor 352, and may send a signal corresponding to the detected light to processor 180. Processor 180 may execute instructions to produce exterior camera digital image of the eye 391.

Tip camera system 300 may include picture-in-picture display 390. Picture-in-picture display 390 may display at least two digital images concurrently. Picture-in-picture display 390 may display tip camera digital image of the eye 291 and exterior camera digital image of the eye 391 concurrently. Tip camera digital image of the eye 291 may be displayed in inset position 395. This may provide a local view and an aerial view of the eye concurrently. Picture-in-picture display 390 may include notch 355. Notch 355 may provide an orientation of tip camera digital image of the eye 291 on exterior camera digital image of the eye 391. This may orient local view of the eye 160 on aerial view of the eye 360. Notch 355 may be a graphical representation displayed by picture-in-picture display 390. The position of notch 355 on exterior camera digital image of the eye may be calculated by processor 180 using information contained in tip camera digital image of the eye 291. Alternatively, endoscope 110 or probe 210 may include gyroscope chip 215. Gyroscope chip 215 may provide the orientation of tip camera digital image of the eye 291 on exterior camera digital image of the eye 391 by indicating true north relative to eye 101. Gyroscope chip 215 may also provide an auto-stabilization mode for picture-in-picture display 390. In auto-stabilization mode, endoscope 110 or probe 210 may be rotated while tip camera digital image of the eye 291 remains stationary.

Figure 4:
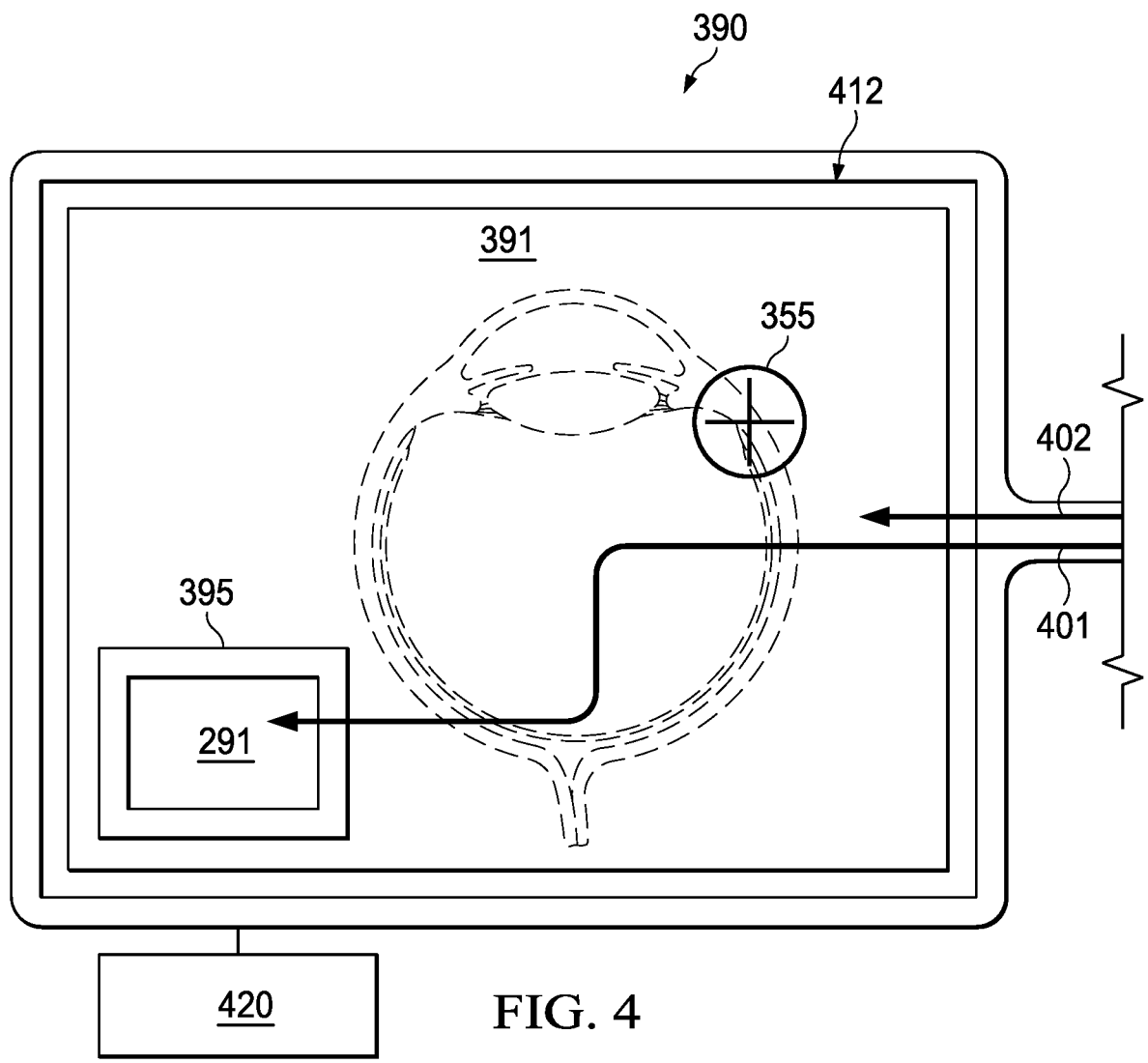
FIG. 4 is a schematic representation of a picture-in-picture display.

Picture-in-picture display 390 in tip camera system 300 may include at least two input signals, which may be tip camera input signal 401 and exterior camera input signal 402 as depicted in FIG. 4. Tip camera input signal 401 may be instructions from processor 180 to display the tip camera digital image of the eye 291, which may include local view of the eye 160. Exterior camera input signal 402 may be instructions from processor 180 to display the exterior camera digital image of the eye 391, which include aerial view of the eye 360. Digital images of the eye displayed by picture-in-picture display 390 may be displayed in color or in monochrome. Picture-in-picture display 390 may display a main image, which may be displayed in full screen position 412 and a picture-in-picture sub image, which may be displayed in inset position 395. Picture-in-picture display 390 may display tip camera digital image of the eye 291 as a picture-in-picture sub image in inset position 395 and exterior camera digital image of the eye 291 as a main image in full screen position 412 as shown, or may display tip camera digital image of the eye 291 as a main image in full screen position 412 and exterior camera digital image of the eye 391 as a picture-in-picture sub image in inset position 395 (not shown). Inset position 395 may be located at the top, bottom, left, right, or any combination thereof, of picture-in-picture display 390. Inset position 395 may be a size that is smaller than full screen position 412. Alternatively, picture-in-picture display may display tip camera digital image of the eye 291 and exterior camera digital image of the eye 391 side-by-side in full screen (not shown). Picture-in-picture display may display tip camera digital image of the eye 291 and exterior camera digital image of the eye 391 in any orientation that provides local view of the eye 160 and aerial view of the eye 360 concurrently.

Picture-in-picture display 390 may display one main image, or may display multiple main images. Picture-in-picture display 390 may display one picture-in-picture sub image, or may display multiple picture-in-picture sub images. Picture-in-picture display 390 may display one or more main images, one or more picture-in-picture sub images, or may display a combination of one or more main images and one or more picture-in-picture sub images. The main image may be tip camera digital image of the eye 291, exterior camera digital image of the eye 391, or any other surgical image, for example an intraoperative optical coherence tomography (OTC) image or another endoscope image. The picture-in-picture sub image may be tip camera digital image of the eye 291, exterior camera digital image of the eye 391, or any other surgical image, for example an intraoperative optical coherence tomography (OTC) image or another endoscope image.

Picture-in-picture display 390 may include any type of screen or projector able to display a digital image of the eye with sufficient resolution to be usable in ophthalmic surgery. For instance, it may include any type of screen or projector used in connection with ophthalmic surgery, including displays of the type used in conventional vitreoretinal surgical systems that present digital images. Picture-in-picture display 390 may display two images for stereoscopic viewing. Picture-in-picture display 390 may be a digital display, a screen, a head up display, a head mounted display, or any combination thereof. Picture-in-picture display 390 may be a flat panel display or an ultra-high-definition 3D flat panel display. Picture-in-picture display 390 may be a 3D organic light-emitting diode (OLED) surgical display. The images displayed on picture-in-picture display 390 may be viewed through a pair of passive, circular polarized glasses. Picture-in-picture display 390 may be a component of a Digitally Assisted Vitreoretinal Surgery ("DAVS") system, or may be a component of a NGENUITY® 3D Visualization System (Novartis AG Corp., Switzerland).

Picture-in-picture display 390 may include a controller 420. Controller 420 may control the digital images of the eye displayed in full screen position 412 and inset position 395, and may control the size, position, relative placement, brightness, resolution, color, or any combination thereof of the digital images. Controller 420 may also control if a single image or multiple images are displayed by picture-in-picture display 390. Processor 180 may vary the on/off status or luminous flux or wavelengths of light of visible light illumination source 340, for example in response to input from controller 420, to improve visibility of eye 101 as viewed on picture-in-picture display 390. Picture-in-picture display 390 may also display a digital image of eye 101 generated by processor 180 or another processor and other information generated by processor 180 or another processor. Such information may include graphic or textual information, such as surgical parameters, surgical modes, flow rates, intraocular pressure, endoscopic video, OCT images, warnings, graphs, color coding or augmented reality information.

The information displayed on picture-in-picture display 390 may not match that displayed on or seen using a surgical microscope. Processor 180 may reformat video made using tip camera 250 or exterior camera 350 for display on picture-in-picture display 390, which may be viewed with circularly polarized glasses, digital oculars, or using a head mounted display.

Figure 5:
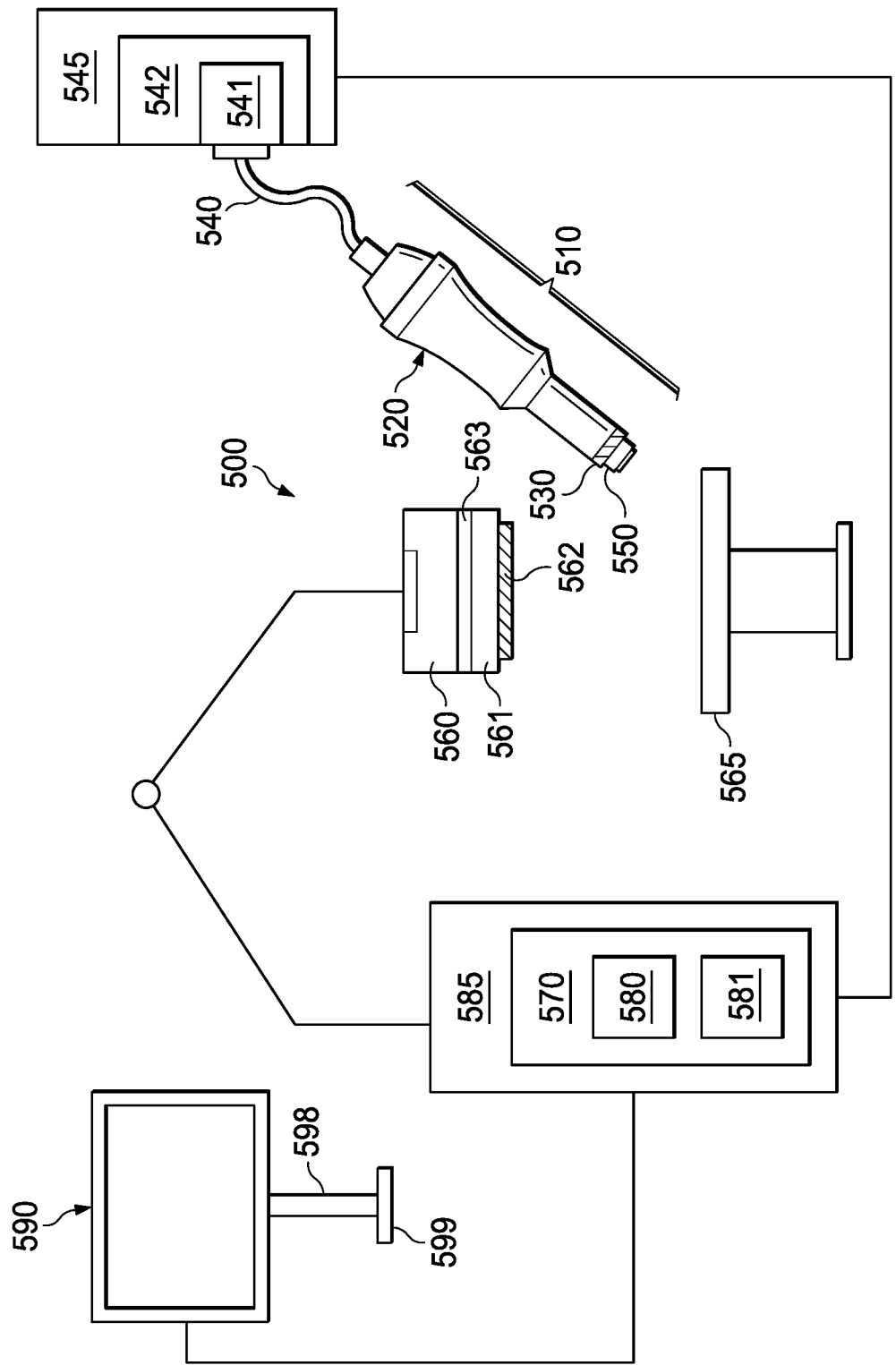
FIG. 5 is a schematic representation of a tip camera system as a component of an NGENUITY® 3D Visualization System (Novartis AG Corp., Switzerland)

Tip camera system 100, tip camera system 200, or tip camera system 300 may be used as a component of the NGENUITY® 3D Visualization System (Novartis AG Corp., Switzerland) in visualization system 500 as depicted in FIG. 5. Visualization system 500 may include probe 510, optical fiber 540, tip camera 550, surgical camera 560, patient table 565, surgical camera system 585, and display 590. Probe 510 may be a probe such as probe 210 and may include probe body 520 and probe tip 530. Optical fiber 540 may be an optical fiber such as optical fiber 240 and may be positioned within probe body 520 and may extend to probe tip 530. Probe 510 may be a vitrectomy probe or an infusion probe. Tip camera 550 may be a tip camera such as tip camera 250 and may be positioned in probe tip 530.

Surgical camera 560 may be positioned above patient table 565. Surgical camera 560 may be an exterior camera, such as exterior camera 350. Surgical camera 560 may also utilize optomechanical focus system 561, zoom system 562, variable working distance system 563. Surgical camera 560 may be communicatively coupled with surgical camera system 585 and display 590. Surgical camera system 585 may include image processing system 570, processor 580, and memory medium 581.

Display 590 may be a head-up display mounted on support member 598 and mount base 599. Support member 598 and mount base 599 may be adjustable to change the distance between display 590 and the surgeon. Display 590 may also be ceiling mounted. Display 590 may be communicatively coupled with surgical camera system 585. Display 590 may be a picture-in-picture display, such as picture-in-picture display 390. In another example, surgical camera 560 may be a 3D HDR camera and display 590 may be a picture-in-picture display, and may be a 3D 4K OLED surgical display. Display 590 may display a 3D surgical image of an eye. Processor 580 may be an ultra-high-speed 3D image processor, which may optimize 3D HDR images in real time.

Optical fiber 540, optical fiber light source 541, and tip camera 550, may be controlled by tip camera control device 542. For example, tip camera control device 542 may adjust the intensity of optical fiber light source 541, the sensitivity of tip camera 550, or any combination thereof. Control device 542 may also control any other variable necessary for visualization for vitreoretinal surgery using visualization system 500. Visualization system 500 may further include surgical console 545. Surgical console 545 may include optical fiber light source 541 and tip camera control device 542. Surgical console 545 may also include any other components necessary for visualization of an eye using tip camera 550 for vitreoretinal surgery.

Surgical console 545 may be communicatively coupled with surgical camera system 585 and display 590. Display 590 may receive information from tip camera 550 via surgical console 545 and surgical camera system 585. Display 590 may receive information from surgical camera 560 via surgical camera system 585. Display 590 may display a digital image of the eye captured by surgical camera 560 and a digital image of the eye captured by tip camera 550 concurrently. This may provide a local view and an aerial view of the eye concurrently.

Figure 6:
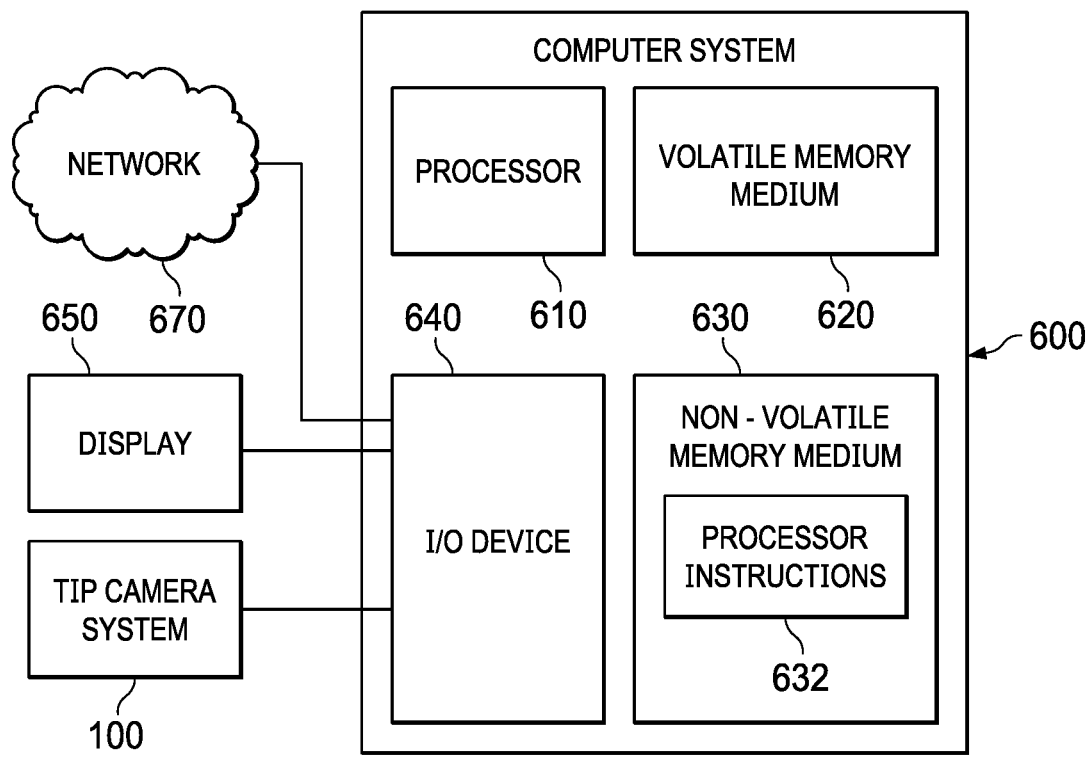
FIG. 6 is a schematic representation of a computer system, including a tip camera system.

Tip camera system 100, tip camera system 200, or tip camera system 300 may be used in combination with a computer system 600, as depicted in FIG. 6. Computer system 600 may include a processor 610, a volatile memory medium 620, a non-volatile memory medium 630, and an input/output (I/O) device 640. Volatile memory medium 620, non-volatile memory medium 630, and (I/O) device 640 may be communicatively coupled to processor 610.

The term "memory medium" may mean a "memory", a "storage device", a "memory device", a "computer-readable medium", and/or a "tangible computer readable storage medium". For example, a memory medium may include, without limitation, storage media such as a direct access storage device, including a hard disk drive, a sequential access storage device, such as a tape disk drive, compact disk (CD), random access memory (RAM), read-only memory (ROM), CD-ROM, digital versatile disc (DVD), electrically erasable programmable read-only memory (EEPROM), flash memory, non-transitory media, or any combination thereof. As shown in FIG. 6, non-volatile memory medium 630 may include processor instructions 632. Processor instructions 632 may be executed by processor 610. In one example, one or more portions of processor instructions 632 may be executed via non-volatile memory medium 630. In another example, one or more portions of processor instructions 632 may be executed via volatile memory medium 620. One or more portions of processor instructions 632 may be transferred to volatile memory medium 620.

Processor 610 may execute processor instructions 632 in implementing at least a portion of one or more systems, one or more flow charts, one or more processes, and/or one or more methods described herein. For example, processor instructions 632 may be configured, coded, and/or encoded with instructions in accordance with at least a portion of one or more systems, one or more flowcharts, one or more methods, and/or one or more processes described herein. Although processor 610 is illustrated as a single processor, processor 610 may be or include multiple processors. One or more of a storage medium and a memory medium may be a software product, a program product, and/or an article of manufacture. For example, the software product, the program product, and/or the article of manufacture may be configured, coded, and/or encoded with instructions, executable by a processor, in accordance with at least a portion of one or more systems, one or more flowcharts, one or more methods, and/or one or more processes described herein.

Processor 610 may include any suitable system, device, or apparatus operable to interpret and execute program instructions, process data, or both stored in a memory medium and/or received via a network. Processor 610 further may include one or more microprocessors, microcontrollers, digital signal processors (DSPs), application specific integrated circuits (ASICs), or other circuitry configured to interpret and execute program instructions, process data, or both.

I/O device 640 may include any instrumentality or instrumentalities, which allow, permit, and/or enable a user to interact with computer system 600 and its associated components by facilitating input from a user and output to a user. Facilitating input from a user may allow the user to manipulate and/or control computer system 600, and facilitating output to a user may allow computer system 600 to indicate effects of the user's manipulation and/or control. For example, I/O device 640 may allow a user to input data, instructions, or both into computer system 600, and otherwise manipulate and/or control computer system 600 and its associated components. I/O devices may include user interface devices, such as a keyboard, a mouse, a touch screen, a joystick, a handheld lens, a tool tracking device, a coordinate input device, or any other I/O device suitable to be used with a system.

I/O device 640 may include one or more buses, one or more serial devices, and/or one or more network interfaces, among others, that may facilitate and/or permit processor 610 to implement at least a portion of one or more systems, processes, and/or methods described herein. In one example, I/O device 640 may include a storage interface that may facilitate and/or permit processor 610 to communicate with an external storage. The storage interface may include one or more of a universal serial bus (USB) interface, a SATA (Serial ATA) interface, a PATA (Parallel ATA) interface, and a small computer system interface (SCSI), among others. In a second example, I/O device 640 may include a network interface that may facilitate and/or permit processor 610 to communicate with a network. I/O device 640 may include one or more of a wireless network interface and a wired network interface. In a third example, I/O device 640 may include one or more of a peripheral component interconnect (PCI) interface, a PCI Express (PCIe) interface, a serial peripheral interconnect (SPI) interface, and an inter-integrated circuit (I2C) interface, among others. In a fourth example, I/O device 640 may include circuitry that may permit processor 610 to communicate data with one or more sensors. In a fifth example, I/O device 640 may facilitate and/or permit processor 610 to communicate data with one or more of a display 650 and tip camera system 100, among others. As shown in FIG. 6, I/O device 640 may be coupled to a network 670. For example, I/O device 640 may include a network interface.

Network 670 may include a wired network, a wireless network, an optical network, or any combination thereof. Network 670 may include and/or be coupled to various types of communications networks. For example, network 670 may include and/or be coupled to a local area network (LAN), a wide area network (WAN), an Internet, a public switched telephone network (PSTN), a cellular telephone network, a satellite telephone network, or any combination thereof. A WAN may include a private WAN, a corporate WAN, a public WAN, or any combination thereof.

Although FIG. 6 illustrates computer system 600 as external to tip camera system 100, tip camera system 100 may include computer system 600. For example, processor 610 may be or include processor 180.

Figure 7:
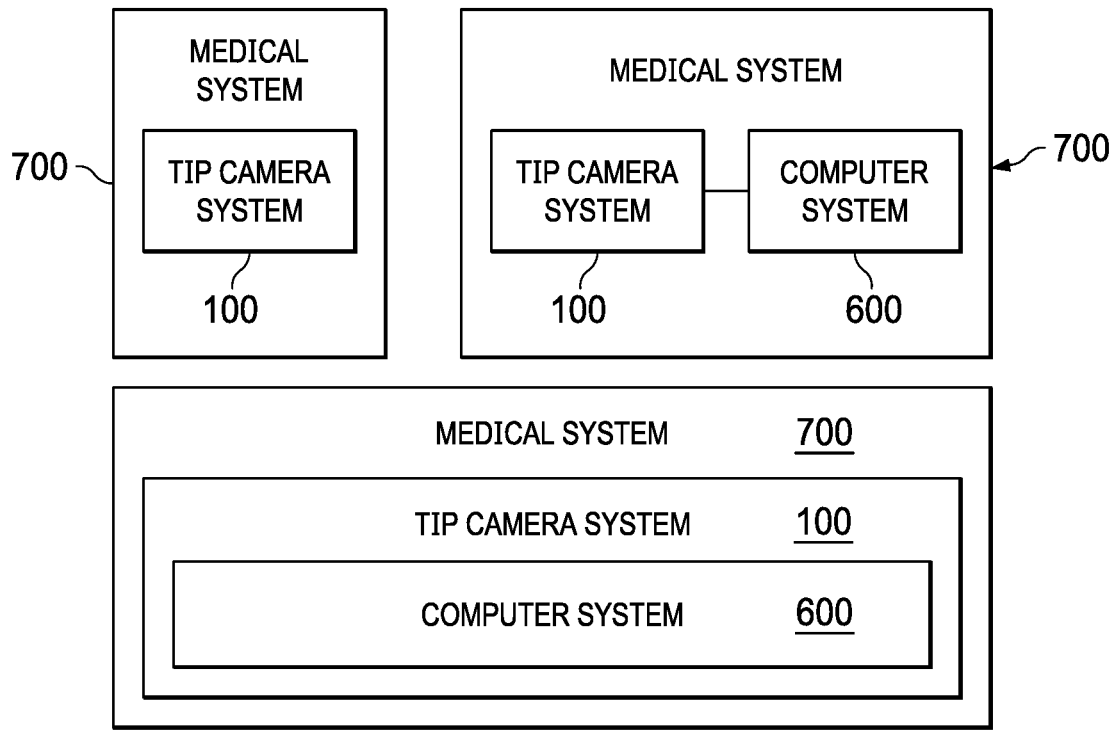
FIG. 7 illustrates various schematic representations of a medical system, including a tip camera system.

FIG. 7 illustrates various examples of medical system 700. A medical system 700 may include tip camera system 100. Alternatively, a medical system 700 may include tip camera system 200 or tip camera system 300. A medical system 700 may include tip camera system 100 and computer system 600. Tip camera system 100 may be communicatively coupled with computer system 600. A medical system 700 may include tip camera system 100, which may include computer system 600.

Figure 8:
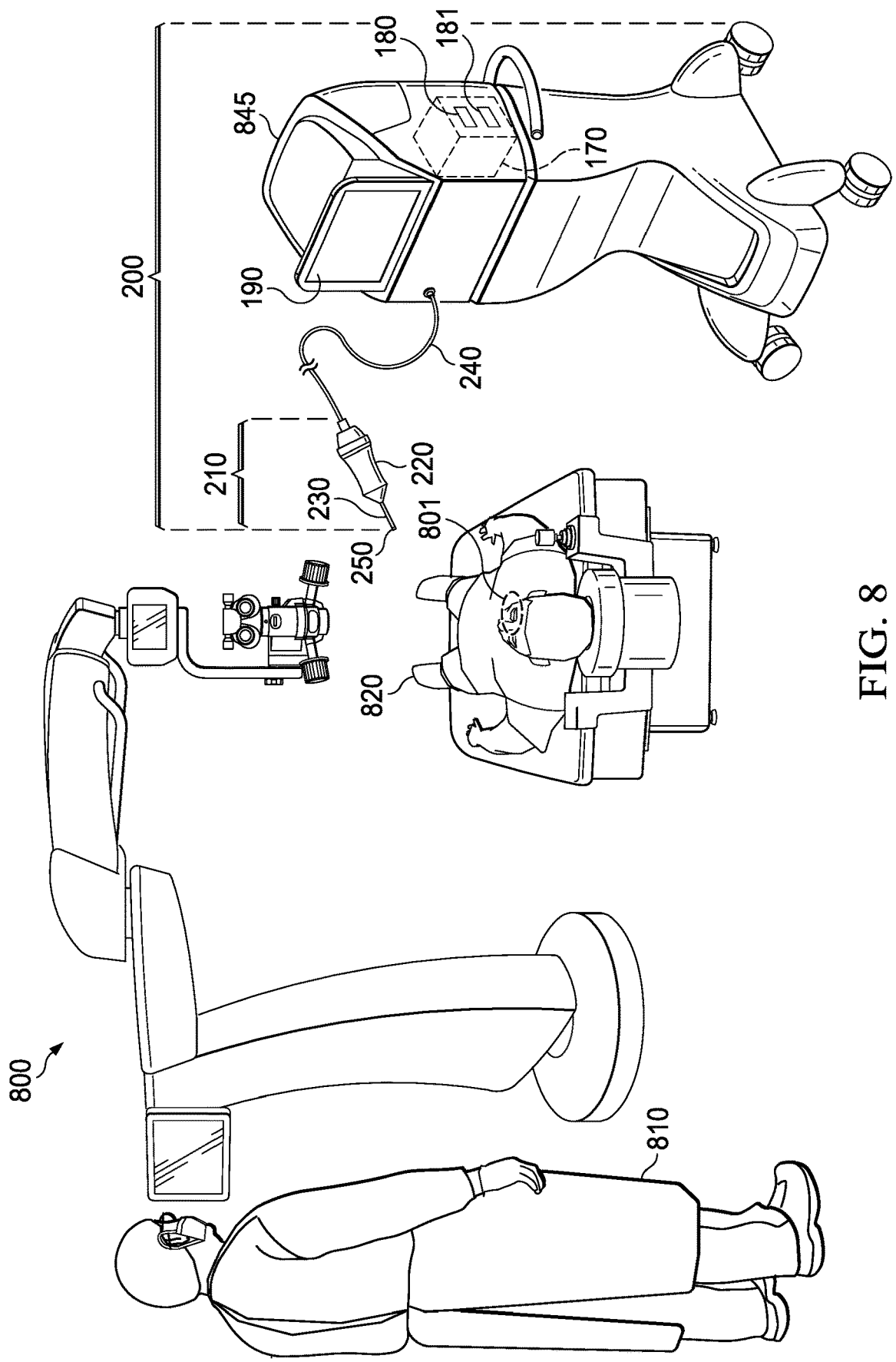
FIG. 8 is an illustration of a medical system, including a tip camera system, a surgeon, and a patient.

Tip camera system 100, tip camera system 200, or tip camera system 300 may be used as a component of medical system 800, as shown in FIG. 8. Medical system 800 may include tip camera system 200, which may be included in surgical console 845. Medical system 800 may include computer system 600. Tip camera system 200 may be communicatively coupled with computer system 600. Surgeon 810 may view a digital image of the interior of eye 801 of patient 820 on display 190 using tip camera 250, which may include a local view of the interior of the eye. Surgeon 810 may view a digital image of eye 801 of patient 820 on microscope integrated display (MID) 830, display 850, or any combination thereof. MID 830, display 850, or any combination thereof, may display an image of eye 801, which may include an aerial view of the eye. Display 190 and display 850 may be combined into a picture-in-picture display, such as picture-in-picture display 390.

Including tip camera system 200 in medical system 800 may provide the surgeon with a local view of the interior of eye 801 and an aerial view of eye 801, which may improve visualization for vitreoretinal surgery compared to visualization without tip camera system 200. Medical system 800 may include a probe 210, an optical fiber 240, a tip camera 250; an image processing system 170, a processor 180; and a memory medium 181, such as those in tip system 200. The memory medium 181 may be coupled to the processor 180, and may include instructions that when executed by the processor, cause the medical system to utilize tip camera system 200 to provide a digital image of a local view the interior of eye 801 of patient 820. Although FIG. 8 illustrates computer system 600 as external to tip camera system 200, tip camera system 200 may include computer system 600. For example, processor 610 may be or include processor 180.

Figure 9:
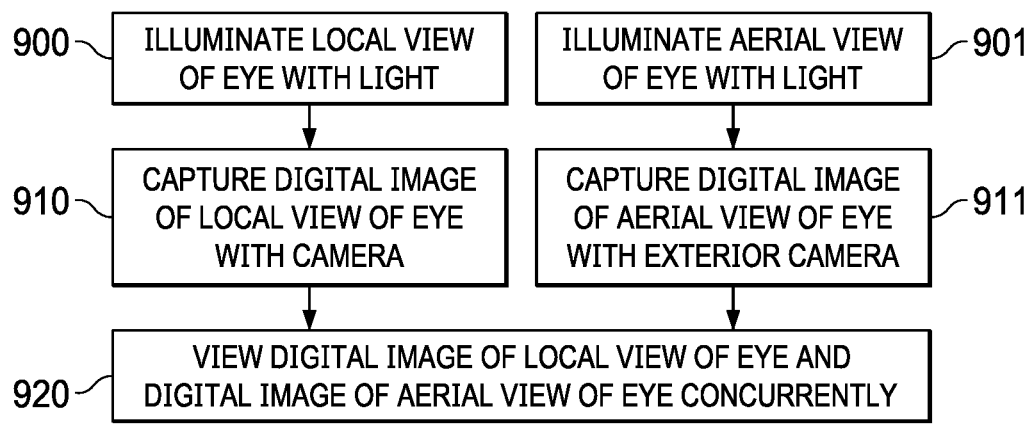
FIG. 9 is a flow diagram illustrating a method of viewing a local view and an aerial view of the eye concurrently to improve visualization for vitreoretinal surgery.

FIG. 9 presents a flow chart for a method of viewing a local view and an aerial view of the eye concurrently to improve visualization for vitreoretinal surgery. In step 900, a local view of an eye, such as local view of the eye 160, is illuminated with light, such as that emitted by illumination fibers in optical fiber 240. In step 910, a camera, such as camera 150 or tip camera 250, is used to capture a digital image of the eye, which may be a digital image of local view of the eye 160. In step 901, an aerial view of an eye, such as aerial view of the eye 360, is illuminated with light, such as that emitted by visible light illumination source 340. In step 911, an exterior camera, such as exterior camera 350, is used to capture an exterior camera digital image of the eye, which may be a digital image of the aerial view of the eye 360. In step 920, a display, such as picture-in-picture display 390, is used to view the digital images of the local view of the eye and the aerial view of the eye concurrently.

In a related method, the optical fiber may be positioned inside a probe, such as probe 210, and the camera may be a tip camera, such as tip camera 250, positioned in a probe tip, such as probe tip 230. In this example, the tip camera may capture a tip camera digital image, such as tip camera digital image of the eye 291, of the local view of the eye.

In a further method, the optical fiber may be positioned inside an endoscope, such as endoscope 110, and may further include image fibers. In this example, the camera may detect light propagated by the image fibers and may capture an endoscope digital image of the local view of the eye, such as endoscope digital image of the eye 191.

The probe tips, tip cameras, and other components described herein may be disposable and may be configured for a single use. Alternatively, they may be sterilizable and configured for multiple uses. In other examples, some components of the tip camera systems disclosed herein may be disposable and some components may be configured for multiple uses.

Tip camera system 100, tip camera system 200, tip camera system 300, picture-in-picture display 390, visualization system 500, computer system 600, medical system 700, medical system 800, and components thereof may be combined with other elements of visualization tools and systems described herein unless clearly mutually exclusive. For instance, tip camera system 100 may be combined with visualization system 500, and may be used with other tip camera systems, visualization systems, computer systems and medical systems described herein.

The above disclosed subject matter is to be considered illustrative, and not restrictive, and the appended claims are intended to cover all such modifications, enhancements, and other embodiments which fall within the true spirit and scope of the present disclosure. For example, although a tip camera system is most commonly needed to improve visualization for vitreoretinal surgery, if it were useful in another procedure, such as a purely diagnostic procedure not otherwise considered to be surgery, the systems and methods described herein may be employed.

The invention claimed is:

1. A tip camera system comprising:
a probe comprising a probe body and a probe tip;
an optical fiber light source;
an optical fiber positioned within the probe body and operable to emit tip light at the probe tip to illuminate an interior of an eye;
a tip camera positioned in the probe tip and comprising a sensor operable to detect tip light emitted by the optical fiber and reflected off the interior of the eye and send a first signal corresponding to the detected tip light to a processor for producing a local view of the interior of the eye having a first magnification level;
a visible light illumination source operable to emit visible light to illuminate an exterior of the eye;
an exterior camera operable to:
detect the visible light emitted by the visible light illumination source and reflected off of the exterior of the eye,
an image processing system comprising the processor and operable to execute instructions to:
produce a tip camera digital image of the local view of the interior of the eye based on the first signal;
detect at least a portion of the tip light illuminating the interior of the eye, and
send a second signal corresponding to the detected visible light and the detected tip light to the processor for producing an aerial view of the exterior of the eye and at least one feature of the interior of the eye, the aerial view having a second magnification level lower than the first magnification level; and
a digital display operable to concurrently display (i) the local view of the interior of the eye having the first magnification level, and (ii) the aerial view of the exterior of the eye and the at least one feature of the interior of the eye, in a picture-in-picture display.

2. The tip camera system of claim 1, wherein the probe is a vitrectomy probe or an infusion probe.

3. The tip camera system of claim 1, wherein the probe tip is insertable into the eye.

4. The tip camera system of claim 1, wherein the sensor is a complementary metal-oxide semiconductor (CMOS) sensor, a monochrome image sensor, a color image sensor, or any combination thereof.

5. The tip camera system of claim 1, wherein the sensor has dimensions in a range of 0.4 to 0.7 mm.

6. The tip camera system of claim 1, wherein the optical fiber light source is a laser source, a narrowband laser source, a broadband laser source, a supercontinuum laser source, an incandescent light bulb, a halogen light bulb, a metal halide light bulb, a xenon light bulb, a mercury vapor light bulb, a light emitting diode (LED), a laser engine, other suitable sources, or any combination thereof.

7. The tip camera system of claim 1, wherein the digital display is a screen, a head up display, a head mounted display, or any combination thereof.

8. The tip camera system of claim 1, wherein the image processing system is further operable to execute instructions to produce an image of a notch on the aerial view of the exterior of the eye indicating a position of the probe within the eye.

9. The tip camera system of claim 1, wherein the at least one feature of the interior of the eye includes a macula, vitreous humor, or retina of the eye.

10. A tip camera system comprising:
an endoscope;
an optical fiber light source;
an optical fiber positioned within the endoscope and operable to emit tip light at a tip of the endoscope to illuminate an interior of an eye;
a camera comprising a sensor operable to detect tip light reflected off the interior of the eye and propagated by the optical fiber and send a first signal corresponding to the detected tip light to a processor for producing a local view of the interior of the eye having a first magnification level;
an image processing system comprising the processor and operable to execute instructions to produce an endoscope digital image of the local view of the interior of the eye based on the first signal;
a visible light illumination source operable to emit visible light to illuminate at least an exterior of the eye;

an exterior camera operable to:
- detect the visible light emitted by the visible light illumination source and reflected off of the exterior of the eye,
- wherein the image processing system further operable to receive a signal describing at least a detected portion of the tip light illuminating the interior of the eye, and send a second signal corresponding to the detected visible light and the detected tip light to the processor for producing an aerial view of the exterior of the eye and at least one feature of the interior of the eye, the aerial view having a second magnification level lower than the first magnification level; and
- a digital display operable to concurrently display (i) the local view of the interior of the eye having the first magnification level, and (ii) the aerial view of the exterior of the eye and the at least one feature of the interior of the eye, in a picture-in-picture display.

11. The tip camera system of claim 10, wherein the optical fiber comprises image fibers and illumination fibers.

12. The tip camera system of claim 10, wherein the endoscope is insertable into the eye.

13. The tip camera system of claim 10, wherein the sensor is a complementary metal-oxide semiconductor (CMOS) sensor, a charge-coupled device (CCD) sensor, a monochrome image sensor, a color image sensor, or any combination thereof.

14. The tip camera system of claim 10, wherein the optical fiber light source is a laser source, a narrowband laser source, a broadband laser source, a supercontinuum laser source, an incandescent light bulb, a halogen light bulb, a metal halide light bulb, a xenon light bulb, a mercury vapor light bulb, a light emitting diode (LED), a laser engine, other suitable sources, or any combination thereof.

15. The tip camera system of claim 10, wherein the digital display is a screen, a head up display, a head mounted display, or any combination thereof.

16. The tip camera system of claim 10, wherein the image processing system is further operable to execute instructions to produce an image of a notch on the aerial view of the exterior of the eye indicating a position of the endoscope within the eye.

* * * * *